US009974491B2

(12) United States Patent
Zhu et al.

(10) Patent No.: US 9,974,491 B2
(45) Date of Patent: May 22, 2018

(54) DETECTING INDICATIONS OF INTRADIALYTIC MORBID EVENTS BY MEASUREMENT OF RELATIVE BLOOD VOLUME, BLOOD PRESSURE AND HEART RATE

(71) Applicant: Fresenius Medical Care Holdings, Inc., Waltham, MA (US)

(72) Inventors: Fansan Zhu, Flushing, NY (US); Peter Kotanko, New York, NY (US); Stephan Thijssen, New York, NY (US); Nathan W. Levin, New York, NY (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 114 days.

(21) Appl. No.: 14/424,005

(22) PCT Filed: Aug. 27, 2013

(86) PCT No.: PCT/US2013/056769
§ 371 (c)(1),
(2) Date: Feb. 25, 2015

(87) PCT Pub. No.: WO2014/035947
PCT Pub. Date: Mar. 6, 2014

(65) Prior Publication Data
US 2015/0208988 A1    Jul. 30, 2015

Related U.S. Application Data

(60) Provisional application No. 61/694,149, filed on Aug. 28, 2012.

(51) Int. Cl.
G08B 21/22     (2006.01)
A61B 5/00      (2006.01)
(Continued)

(52) U.S. Cl.
CPC .............. *A61B 5/746* (2013.01); *A61B 5/021* (2013.01); *A61M 1/16* (2013.01); *A61M 1/1603* (2014.02);
(Continued)

(58) Field of Classification Search
CPC .......... A61B 5/021; A61B 5/746; A61M 1/16; A61M 1/1603; A61M 1/1615;
(Continued)

(56) References Cited

U.S. PATENT DOCUMENTS 4,284,502 A * 8/1981 Kramer ............... A61M 1/3441
                                                 210/321.65
4,718,891 A   1/1988 Lipps
(Continued)

FOREIGN PATENT DOCUMENTS

| EP | 2469431 A1 | 6/2012 |
|----|------------|--------|
| WO | WO 2011/080190 A1 | 7/2011 |
| WO | WO 2014/035947 A1 | 3/2014 |

OTHER PUBLICATIONS

Notification Concerning Transmittal of International Preliminary Report on Patentability for International Application No. PCT/US2013/056769; dated Mar. 12, 2015 entitled "Detecting Indications of Intradialytic Morbid Events by Measurement of Relative Blood Volume, Blood Pressure and Heart Rate."
(Continued)

*Primary Examiner* — Daniel Previl
(74) *Attorney, Agent, or Firm* — Hamilton, Brook, Smith & Reynolds, P.C.

(57) ABSTRACT

A method of detecting an indication of a potential intradialytic morbid event (IME) by monitoring a patient's condition during excess fluid removal by ultrafiltration during a hemodialysis treatment includes determining the patient's relative blood volume (RBV), and removing a portion of the
(Continued)

volume of excess fluid from blood of the patient at an initial ultrafiltration rate while periodically monitoring a second derivative over time of the relative blood volume (SDRBV). The method then includes continuing to remove excess fluid from blood of the patient at the same ultrafilration rate, or, optionally, incrementally increasing the ultrafiltration rate. The method further includes triggering an alarm for an IME for the patient if the SDRBV is in a range of between a low SDRBV alarm level and a high SDRBV alarm level, and, alternatively or additionally monitoring the patient's normalized blood pressure ratio, and taking a remedial action if the alarm is triggered.

32 Claims, 11 Drawing Sheets

(51) Int. Cl.
*A61B 5/021* (2006.01)
*A61M 1/16* (2006.01)
*A61M 1/34* (2006.01)
*A61M 1/36* (2006.01)

(52) U.S. Cl.
CPC .......... *A61M 1/1615* (2014.02); *A61M 1/341* (2014.02); *A61M 1/3413* (2013.01); *A61M 1/3609* (2014.02); *A61M 2230/06* (2013.01); *A61M 2230/30* (2013.01)

(58) Field of Classification Search
CPC .. A61M 1/341; A61M 1/3413; A61M 1/3609; A61M 2230/06; A61M 2230/30
USPC .......... 340/573.1, 573.7, 626, 679, 680, 3.1, 340/292, 286.07, 286.11, 286.12, 309.4
See application file for complete search history.

(56) References Cited

U.S. PATENT DOCUMENTS

| | | | |
|---|---|---|---|
| 5,803,908 A * | 9/1998 | Steuer | A61B 5/14535 600/314 |
| 6,527,728 B2 | 3/2003 | Zhang | |
| 6,623,470 B2 | 9/2003 | Munis et al. | |
| 6,775,577 B2 | 8/2004 | Crnkovich et al. | |
| 7,570,979 B2 | 8/2009 | Cooper | |
| 8,060,190 B2 | 11/2011 | Sömmo et al. | |
| 2002/0055672 A1 | 5/2002 | Zhang | |
| 2007/0215545 A1 | 9/2007 | Bissler et al. | |
| 2010/0094158 A1 | 4/2010 | Solem et al. | |
| 2011/0036773 A1* | 2/2011 | Moissl | A61M 1/3639 210/646 |
| 2011/0270058 A1* | 11/2011 | Price | A61B 5/021 600/324 |
| 2012/0016246 A1 | 1/2012 | Sandgaard | |
| 2012/0203476 A1* | 8/2012 | Dam | A61B 5/14535 702/48 |
| 2013/0331712 A1* | 12/2013 | Moissl | A61M 1/16 600/483 |

OTHER PUBLICATIONS

Notification of Transmittal of the International Search Report and the Written Opinion of the International Searching Authority, or The Declaration for International Application No. PCT/US2013/056769; dated Jan. 10, 2014 entitled "Detecting Indications of Intradialytic Morbid Events by Measurement of Relative Blood Volume, Blood Pressure and Heart Rate."

Zhu, F., et al., "Prediction of Intradialytic Morbid Events in Hemodialysis Patients by Monitoring the Second Derivative of Relative Blood Volume", *34th Annual International Conference of the IEEE EMBS*: San Diego, California; 1226-1229 (2012).

* cited by examiner

DETECTING INDICATIONS OF INTRADIALYTIC MORBID EVENTS BY MEASUREMENT OF RELATIVE BLOOD VOLUME, BLOOD PRESSURE AND HEART RATE

RELATED APPLICATIONS

This application is the U.S. National Stage of International Application No. PCT/US2013/056769, filed Aug. 27, 2013, which designates the U.S., published in English, and claims the benefit of U.S. Provisional Application No. 61/694,149, filed on Aug. 28, 2012. The entire teachings of the above applications are incorporated herein by reference.

BACKGROUND OF THE INVENTION

Prediction of an intradialytic morbid event (IME) during hemodialysis (HD) is difficult in clinical practice because no reliable and accurate technique is available. An IME is typically defined by a patient's systolic blood pressure (SBP) decreasing to less than about 90 mmHg and a heart rate (HR) greater than about 100 beats/min with muscle cramps, dizziness or fainting of the patient, often leading to the need to discontinue ultrafiltration before the end of an HD treatment. Monitoring of relative blood volume (RBV) by means of a device such as CRIT-LINE™ (Hema Metrics, Kaysville, Utah, see U.S. Pat. No. 5,803,908) or blood volume monitor (BVM, Fresenius AG, Germany) has been used to assess critical thresholds of RBV which may indicate the risk of an IME. See C. Barth, W. Boer, D. Garzoni, T. Kuenzi, W. Ries, R. Schaefer, D. Schneditz, T. Tsobanelis, F. van der Sande, R. Wojke, H. Schilling, and J. Passlick-Deetjen, "Characteristics of hypotension-prone haemodialysis patients: is there a critical relative blood volume?," Nephrol Dial Transplant, vol. 18, pp. 1353-60, July 2003. However, the relationship between a change in RBV and an IME depends on multiple factors including, but not limited to, ultrafiltration rate (UFR), degree of fluid overload, plasma refilling rate, and autonomic nervous system control. For this reason, measurement of changes in RBV alone fails to reliably predict an IME. See D. N. Reddan, L. A. Szczech, V. Hasselblad, E. G. Lowrie, R. M. Lindsay, J. Himmelfarb, R. D. Toto, J. Stivelman, J. F. Winchester, L. A. Zillman, R. M. Califf, and W. F. Owen, Jr., "Intradialytic blood volume monitoring in ambulatory hemodialysis patients: a randomized trial," J Am Soc Nephrol, vol. 16, pp. 2162-9, July 2005.

Therefore, there is a need for a more reliable method of predicting the occurrence of an IME in a patient having excess fluid removed by ultrafiltration during a hemodialysis treatment.

SUMMARY OF THE INVENTION

In one embodiment, a method of detecting an indication of a potential intradialytic morbid event (IME) by monitoring a patient's condition during excess fluid removal by ultrafiltration during a hemodialysis treatment includes establishing an initial ultrafiltration rate of fluid removal, determining the patient's relative blood volume (RBV), and removing a portion of the volume of excess fluid from blood of the patient at the initial ultrafiltration rate while periodically monitoring the second derivative of the patient's relative blood volume (SDRBV) over time, which can be calculated from $d^2(RBV)/dt^2$.

In a preferred embodiment, the method can further include monitoring the patient's normalized blood pressure ratio, and triggering an alarm for a potential IME for the patient if the SDRBV is in a range of between a low SDRBV alarm level and a high SDRBV alarm level and if the normalized blood pressure ratio is less than a ratio alarm level.

In an alternative embodiment, the method can include independently monitoring the normalized blood pressure ratio, and triggering an alarm for a potential IME for the patient if the ratio is less than a ratio alarm level.

The low SDRBV alarm level can be about $-0.08\%/min^2$. The high SDRBV alarm level can be about $-0.035\%/min^2$. The ratio alarm level can be about 0.019 min/beat for a diastolic blood pressure greater than 50 mmHg, or about 0.02 min/beat for a diastolic blood pressure less than 50 mmHg.

The method then includes continuing to remove excess fluid from blood of the patient at the same ultrafiltration rate, or, optionally, incrementally increasing the ultrafiltration rate. The method then includes taking a remedial action if the alarm is triggered. The remedial action can be decreasing the ultrafiltration rate, infusion of fluid into the patient, compressing lower extremities of the patient, and/or changing the position of the patient, such as placing the patient in the Trendelenburg position or raising the patient's legs, or a combination of these remedial actions.

In another embodiment, a method of detecting an indication of a potential intradialytic morbid event (IME) by monitoring a patient's condition during excess fluid removal by ultrafiltration during a hemodialysis treatment includes the computer implemented steps of establishing an initial ultrafiltration rate of fluid removal, determining the patient's relative blood volume (RBV), and removing a portion of the volume of excess fluid from blood of the patient at the initial ultrafiltration rate while periodically monitoring the second derivative of the patient's relative blood volume (SDRBV) over time, which can be calculated from $d^2(RBV)/dt^2$. The method then includes continuing to remove excess fluid from blood of the patient at the same ultrafiltration rate, or, optionally, incrementally increasing the ultrafiltration rate.

In a preferred embodiment, the computer implemented method can further include monitoring the patient's normalized blood pressure ratio, and triggering an alarm for a potential IME for the patient if the SDRBV is in a range of between a low SDRBV alarm level and a high SDRBV alarm level and if the normalized blood pressure ratio is less than a ratio alarm level.

Some of the above methods can be incorporated into a hemodialysis system and/or procedure, and include many advantages including the ability to reliably predict an IME prior to its occurrence in a timely fashion and thereby prevent its occurrence while optimizing the removal of excess fluid from a hemodialysis patient.

BRIEF DESCRIPTION OF THE DRAWINGS

The foregoing will be apparent from the following more particular description of example embodiments of the invention, as illustrated in the accompanying drawings. The drawings are not necessarily to scale, emphasis instead being placed upon illustrating embodiments of the present invention.

DETAILED DESCRIPTION OF THE INVENTION

Figure 1A:
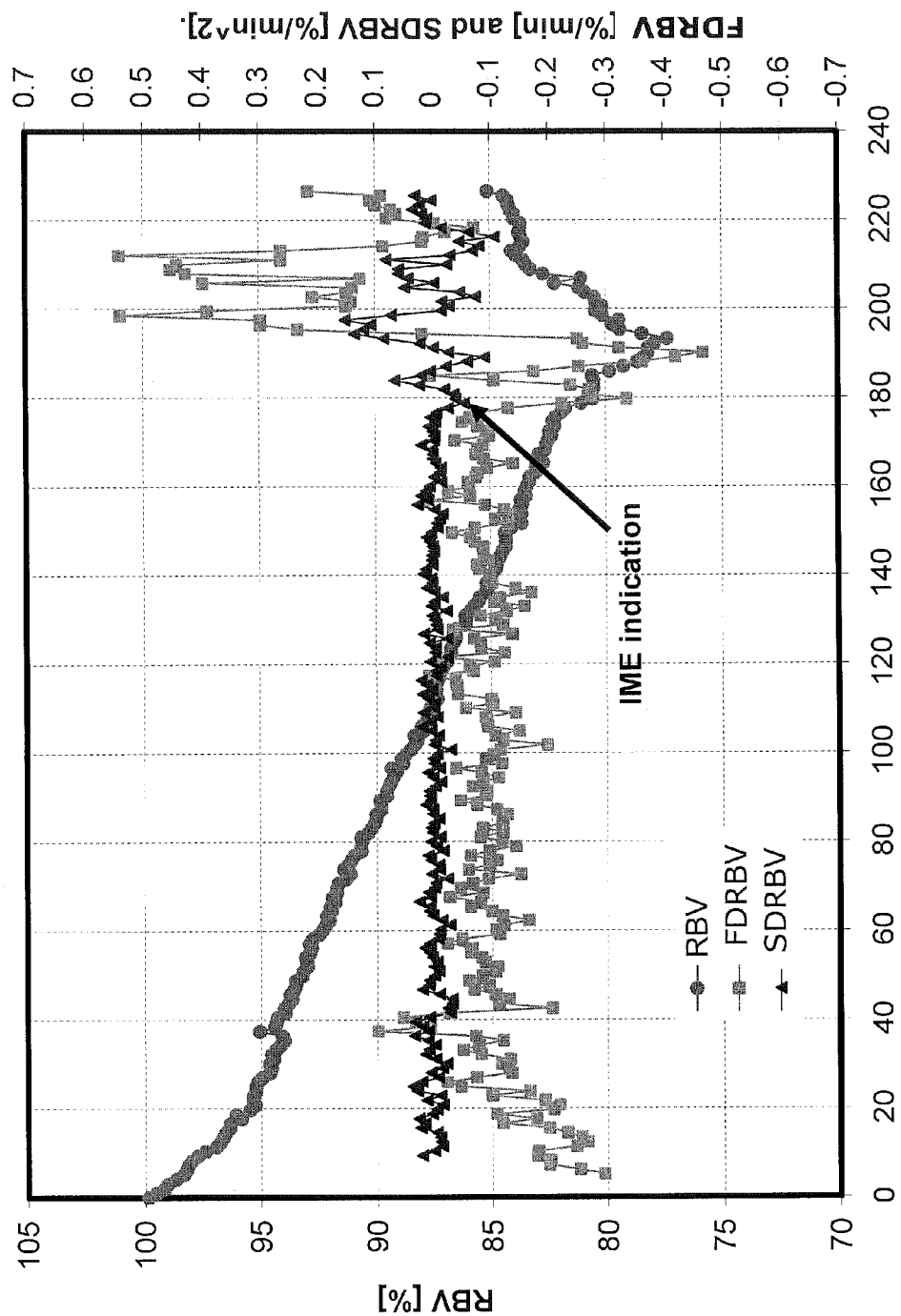
FIG. 1A is a graph of relative blood volume percent RBV [%] (left axis) and the first derivative of RBV, FDRBV [%/min] and second derivative of RBV, SDRBV [%/min$^2$] (right axis) as a function of time [min] illustrating data from a hemodialysis patient that experienced an IME. The line of circles represents the patient's RBV curve, the line of squares represents the patient's FDRBV, and the line of triangles represents the patient's SDRBV as a function of time. Variation in the data is reduced with SDRBV. The patient had an IME at 180 min of hemodialysis and ultrafiltration was stopped at 190 min due to hypotensive symptoms.
Figure 1B:
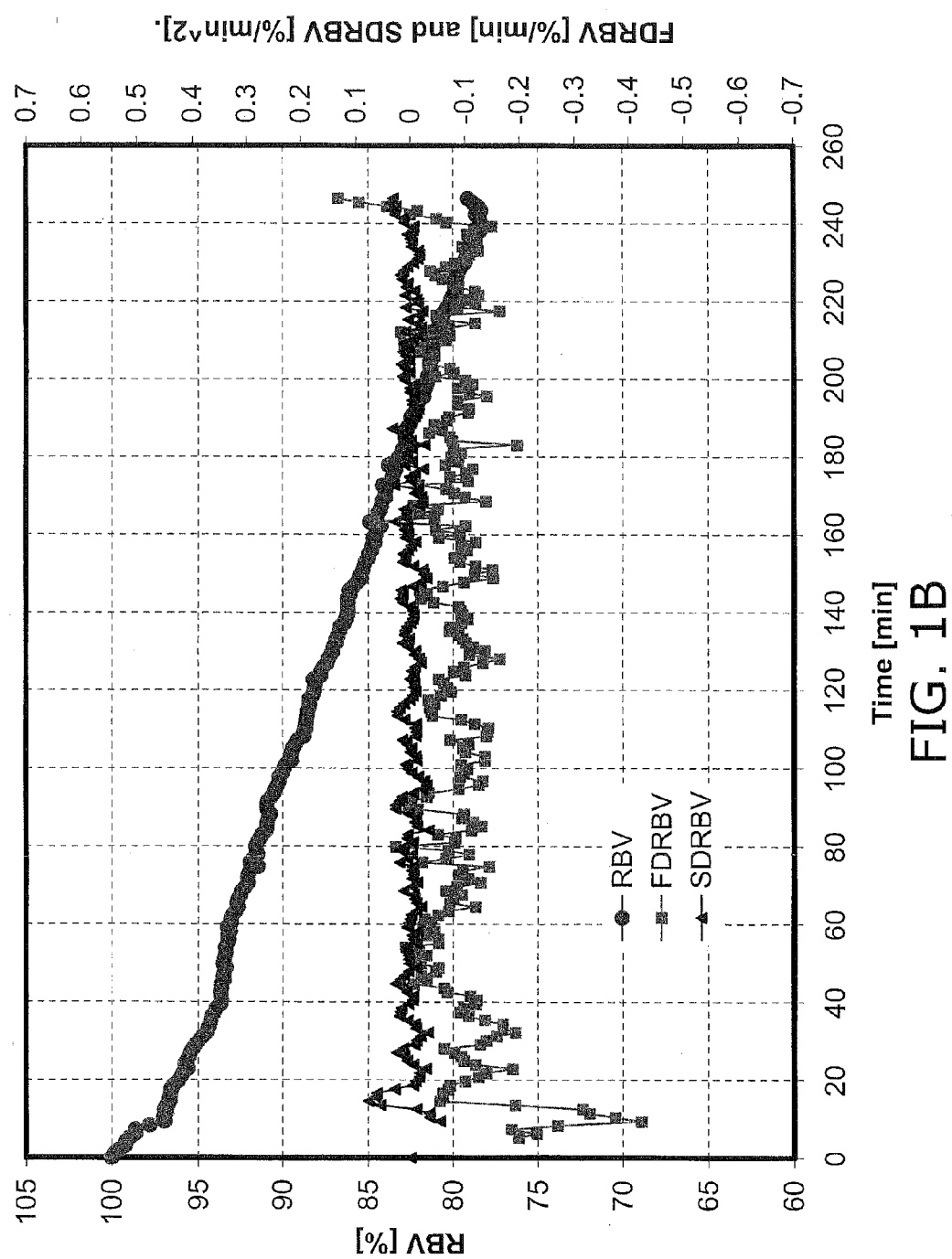
FIG. 1B is a graph of relative blood volume percent RBV [%] (left axis) and first derivative of RBV, FDRBV [%/min] and second derivative of RBV, SDRBV [%/min$^2$] (right axis) as a function of time [min] for a hemodialysis patient without an IME during removal of excess fluid by ultrafiltration.

In one embodiment, a method of detecting an indication of a potential intradialytic morbid event (IME) by monitoring a patient's condition during excess fluid removal by ultrafiltration during a hemodialysis treatment includes establishing an initial ultrafiltration rate (UFR) of fluid removal, determining the patient's relative blood volume (RBV), and removing a portion of the volume of excess fluid from blood of the patient at the initial ultrafiltration rate while periodically monitoring the second derivative of the patient's relative blood volume (SDRBV) over time, which can be calculated from $d^2(RBV)/dt^2$. Monitoring over time can be, for example, every 5 minutes. The method then includes continuing to remove excess fluid from blood of the patient at the same ultrafiltration rate, or, optionally, incrementally increasing the ultrafiltration rate by, for example, about 10%. The ultrafiltration rate can be, for example, increased up to the rate required to remove the clinically indicated (i.e., physician prescribed) amount of excess fluid from the patient over the hemodialysis treatment time.

In a preferred embodiment, the method can further include monitoring the patient's normalized blood pressure ratio, and triggering an alarm for a potential IME for the patient if the SDRBV is in a range of between a low SDRBV alarm level and a high SDRBV alarm level and if the normalized blood pressure ratio is less than a ratio alarm level. The method then includes taking a remedial action if the alarm is triggered. The low SDRBV alarm level can be about $-0.08\%/min^2$. The high SDRBV alarm level can be about $-0.035\%/min^2$. The normalized blood pressure ratio (SDH) is calculated using the patient's systolic blood pressure (SBP), diastolic blood pressure (DBP), and heart rate (HR), and calculating the ratio SDH=(SBP/DBP)/HR.

In an alternative embodiment, the method can include independently monitoring the ratio, and triggering an alarm for a potential IME for the patient if the ratio is less than a ratio alarm level. The ratio alarm level can be about 0.019 min/beat for a diastolic blood pressure greater than 50 mmHg, or about 0.02 min/beat for a diastolic blood pressure less than 50 mmHg. The ratio can be monitored periodically, such as, for example, every 10 minutes.

The remedial action can be decreasing the ultrafiltration rate (e.g., by about 5-10%), or infusion of fluid into the patient, or compressing lower extremities of the patient (e.g., by application of a compression device, such as, for example Kendall 7325, Covidien, Mansfield, Mass.), or changing the position of the patient, such as placing the patient in the Trendelenburg position, or raising the patient's legs, or a combination of these remedial actions. Some of the above methods can be incorporated into a hemodialysis system and/or procedure. See Handbook of Dialysis, J. T. Daugirdas, P. G. Blake, and T. S. Ing, 4$^{th}$ Edition, p. 59-78 (2007).

Two principal criteria to predict IME are considered in the present application: (a) the second derivative of RBV and (b) blood pressure (BP) combined with heart rate (HR).

1. Second Derivative of RBV Criterion

Using the FDRBV or slope of the RBV (d(RBV)/dt) in the first 30 min of HD to predict an IME has been discussed in previous publications. See e.g., Titapiccolo, et al, 32nd Annual International Conference of the IEEE EMBS, 2010. A recent study showed that the slope of the RBV in the first 30 min of hemodialysis is significantly higher than at the end of treatment in patients that develop an IME. See E. Seibert, F. Zhu, M. K. Kuhlmann, R. Henson, A. M. Oribello, M. Girndt, P. Kotanko, and N. W. Levin, "Slope analysis of blood volume and calf bioimpedance monitoring in hemodialysis patients," *Nephrol. Dial. Transplant.*, 27(12):4430-6, (2012). As shown in Eq.1, the first derivative or slope of RBV (FDRBV or sRBV) indicates the difference between plasma refilling rate (PRR ml/min) and ultrafiltration rate (UFR ml/min). In principle, an IME might occur when the PRR is less than the UFR. In practice, however, an individual UFR may not be constant even in the same treatment so that the FDRBV is difficult to standardize sufficiently to be useful in clinical practice. Therefore, a method to use the second derivative of RBV (SDRBV) to calculate change in PRR (Eq. 2) is disclosed herein. The major advantage of this method is that it is independently monitoring the change in PRR.

$$\frac{dRBV}{dt} = \frac{1}{BV_0}[PRR - UFR] \qquad \text{Eq. 1}$$

$$\frac{d^2RBV}{dt^2} = \frac{1}{BV_0}d[PRR - UFR]/dt = \frac{dPRR/dt}{BV_0} \qquad \text{Eq. 2}$$

In Eq. 1, RBV represents relative blood volume calculated by change in absolute blood volume (BV) divided by initial $BV_0$, where PRR represents plasma refilling rate. In Eq. 2, the second derivative of RBV (SDRBV) can be written as the derivative of RBV slope ($d^2(RBV)/dt^2$, %/min$^2$), which represents change in PRR, with UFR and $BV_0$ considered constant. To simplify notation, SDRBV will be used to represent the second derivative of RBV in this application.

2. SDH Criterion

The SDH ratio is defined as the ratio of systolic BP (SBP; mmHg) to diastolic BP (DBP; mmHg) divided by heart rate (HR; beat/min) as follows:

SDH [min/beat]=(SBP/DBP)/HR    Eq.3

Figure 2:
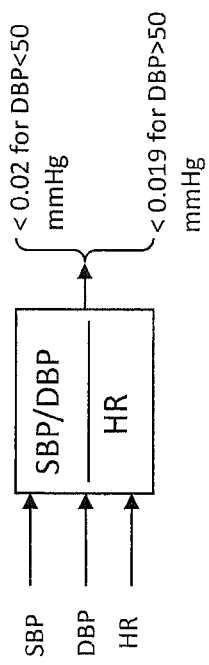
FIG. 2 is a flow chart of the integration of systolic blood pressure (SBP), diastolic blood pressure (DBP), and heart rate (HR) according to this invention.

The integrated assessment of SBP, DBP, and HR is illustrated in FIG. 2. Note that the interpretation of SDH depends on the level of DBP, so that with DBP≥50 mmHg the $SDH_{Threshold}$ is 0.019 [beat/min], and with DBP<50 mmHg the $SDH_{Threshold}$ is 0.02 [beat/min]. For example, in a patient with DBP of 90 mmHg and a SDH of 0.015 [beat/min] the risk of IME is higher compared to a patient with the same DBP but an SDH of 0.025 [beat/min].

Without wishing to be bound by any particular theory, the rationale for the SDH ratio is thought to be as follows: in the majority of IMEs (and per definition in all cases of intradialytic hypotension (IDH)), blood pressure (BP) is reduced. Physiologically, an initial drop in BP is counteracted by a rise in HR in an effort to maintain cardiac output and BP; actually, the relative increase in HR is more pronounced than the relative decrease in BP. For this reason a ratio of BP over HR may provide an augmented signal. However, levels of absolute BP vary greatly among HD patients (SBP: 70-250 mmHg; DBP: 40-150 mmHg). The ratio of SBP to DBP shows less variability. In a recent study, it was found that the ratio of SBP to DBP at beginning of HD differs between patients with IME (SBP/DBP: 0.024±0.004) and without (0.025±0.005) IME (Zhu et al. 49th ERA-EDTA Congress, 2012). Moreover, the differentiation between patients with and without an IME can be improved by the use of SDH in addition to the SDRBV discussed above.

3. A Flowchart Combining SDRBV and SDH

It is general knowledge that rapid reduction of blood volume by a higher UFR is the major cause of an IME. SDRBV can show the change in relative blood volume as (%/min$^2$), while the SDH indicates individual tolerance for an IME according to information about blood pressure and heart rate. Since reduction of blood volume is the primary factor for a possible IME, monitoring RBV slope is the first criterion. If the SDRBV is in the range between the values of the $SDRBV_i$ criteria ($-0.08 < SDRBV_i < 0.035$, i represents any time) at the time i, and $SDH_i$ is less than the $SDH_{Threshold}$ ($SDH_i < SDH_{Threshold}$), then an IME can be predicted.

Figure 3:
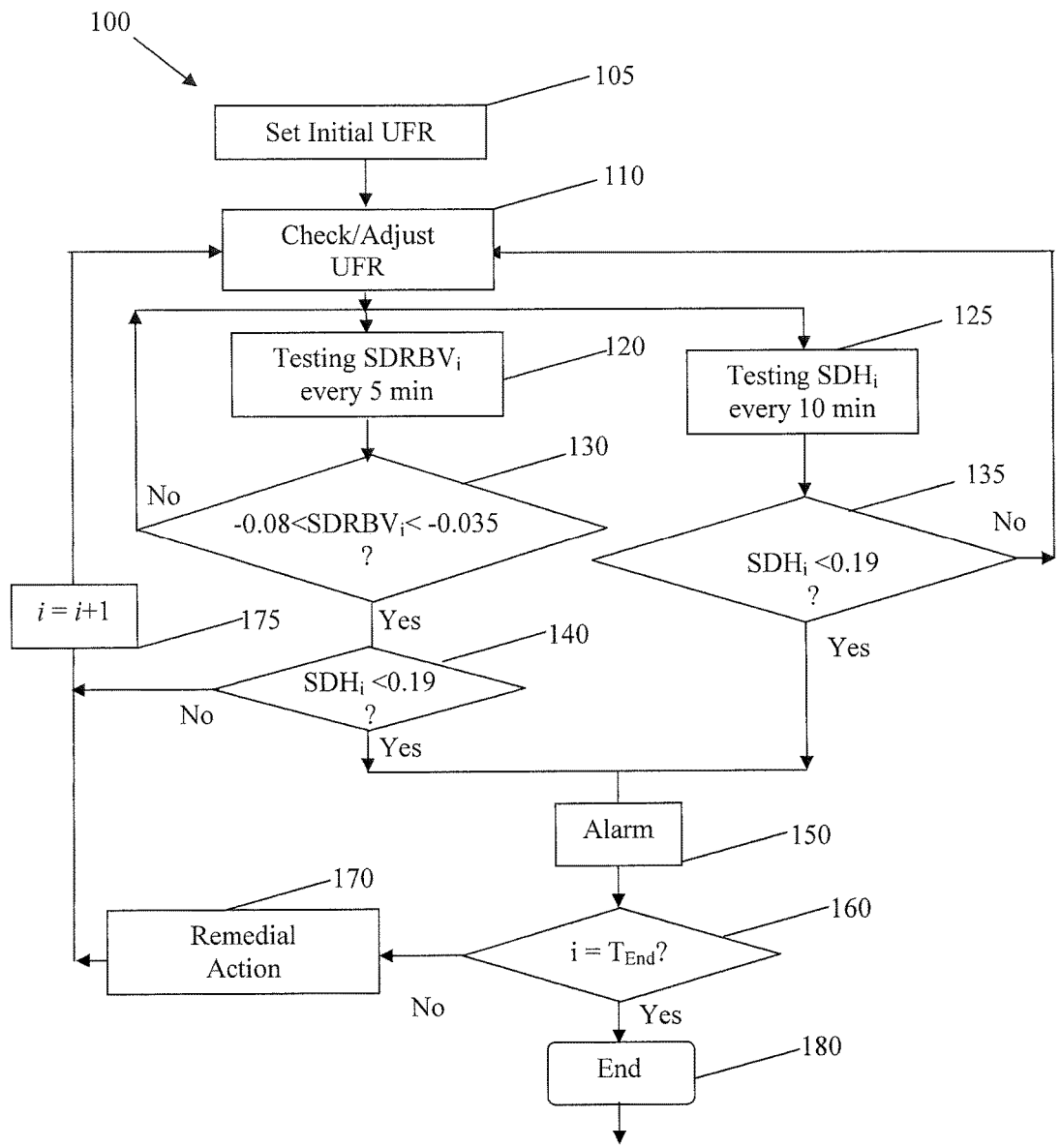
FIG. 3 is a flowchart used for predicting an IME with two criteria according to this invention. The first criteria includes monitoring RBV and calculating SDRBV every 5 minutes. If $-0.08 < SDRBV_i < -0.035$ at ith minutes, then for the second criteria, SBP, DBP and HR are immediately measured and SDH is calculated. If $SDH_i < SDH_{Threshold}$, a signal for predicting an IME will be sent. SDH is also monitored every 10 minutes. If $SDH < SDH_{Threshold}$, a signal for predicting an IME will be sent.

FIG. 3 illustrates a flowchart for prediction of a potential IME during the treatment. The criteria of SDH and SDRBV are observed from experimental data. A person of skill in the art can obtain revised numerical values for the SDH and SDRBV criteria from additional and/or different experimental data. As shown in FIG. 3, a method 100 of detecting an indication of a potential intradialytic morbid event (IME) in a patient having excess fluid removed by ultrafiltration during a hemodialysis treatment includes setting an initial UFR at step 105, then, at step 110, checking the ultrafiltration rate and optionally adjusting the ultrafiltration rate as clinically indicated. The method then includes at step 120 determining the patient's relative blood volume (RBV) periodically (e.g., every 5 minutes), monitoring a second derivative of the relative blood volume (SDRBV) over time, which can be calculated from $d^2(RBV)/dt^2$. If, at step 130, the SDRBV is in a range of between a low SDRBV alarm level and a high SDRBV alarm level, and, at step 140, if the patient's normalized blood pressure ratio SDH is less than a SDH alarm level, wherein the SDH is calculated from the patient's systolic blood pressure (SBP), diastolic blood pressure (DBP), and heart rate (HR), using the formula SDH=(SBP/DBP)/HR, then the method includes triggering an alarm at step 150 and, if, at step 160, the treatment time is not at an end, taking a remedial action at step 170 and incrementing the time i at step 175 and continuing to check and/or adjust the UFR at step 110 as appropriate. Adjusting the UFR can include increasing or decreasing the UFR (e.g., by about 10%). As shown in FIG. 3, the treatment ends at step 180 once the treatment time is reached. The low SDRBV alarm level can be about $-0.08\%/\text{min}^2$. The high SDRBV alarm level can be about $-0.035\%/\text{min}^2$. The SDH alarm level can be about 0.019 min/beat for a diastolic blood pressure greater than 50 mmHg, or about 0.02 min/beat for a diastolic blood pressure less than 50 mmHg.

The method 100 can further include periodically monitoring, at step 125, the patient's systolic blood pressure (SBP), diastolic blood pressure (DBP), heart rate (HR), and a normalized blood pressure ratio SDH=(SBP/DBP)/HR, and, at step 135, if the SDH is less than a SDH alarm level, triggering an alarm at step 150 for an IME for the patient, as described above. At step 125, the SDH can be monitored periodically, such as, for example, every 10 minutes.

4. Pre-Processing of RBV Data

RBV raw data can be influenced by several factors not associated with the change in the plasma refilling rate. One of the potential interferences is a rapid change in the RBV curve which could result from sudden vasoconstriction, shown as high frequency noise. To reduce this noise, a low-pass filter with a moving average method was used to smooth the RBV curve before calculation of the first derivative of the RBV (FDRBV) and the second derivative of the RBV (SDRBV). The other source of error from RBV raw data was a sudden change in body position of the patient during the measurement. This error can produce about $-0.08$ to $-0.1\%/\text{min}^2$ variation in the curve of SDRBV. To reduce this error, when the value of SDRBV was less than $-0.08$, it was considered as interference and was not utilized for data analysis. Accordingly, in this study the criterion for IME has been set as a range: $-0.08 < SDRBV_i < -0.035$, %/min$^2$. A person of skill in the art can obtain different numerical values for the SDRBV and SDH alarm levels from additional studies and error analysis.

5. Computer Implementation

In another embodiment, a method of detecting an indication of a potential intradialytic morbid event (IME) by monitoring a patient's condition during excess fluid removal by ultrafiltration during a hemodialysis treatment includes the computer implemented steps of establishing an initial ultrafiltration rate of fluid removal, determining the patient's relative blood volume (RBV), and removing a portion of the volume of excess fluid from blood of the patient at the initial ultrafiltration rate while periodically monitoring the second derivative of the patient's relative blood volume (SDRBV) over time, which can be calculated from $d^2(RBV)/dt^2$. The method then includes continuing to remove excess fluid from blood of the patient at the same ultrafiltration rate, or, optionally, incrementally increasing the ultrafiltration rate.

In a preferred embodiment, the method can further include monitoring the patient's normalized blood pressure ratio, and triggering an alarm for a potential IME for the patient if the SDRBV is in a range of between a low SDRBV alarm level and a high SDRBV alarm level and if the normalized blood pressure ratio is less than a ratio alarm level.

Figure 10:
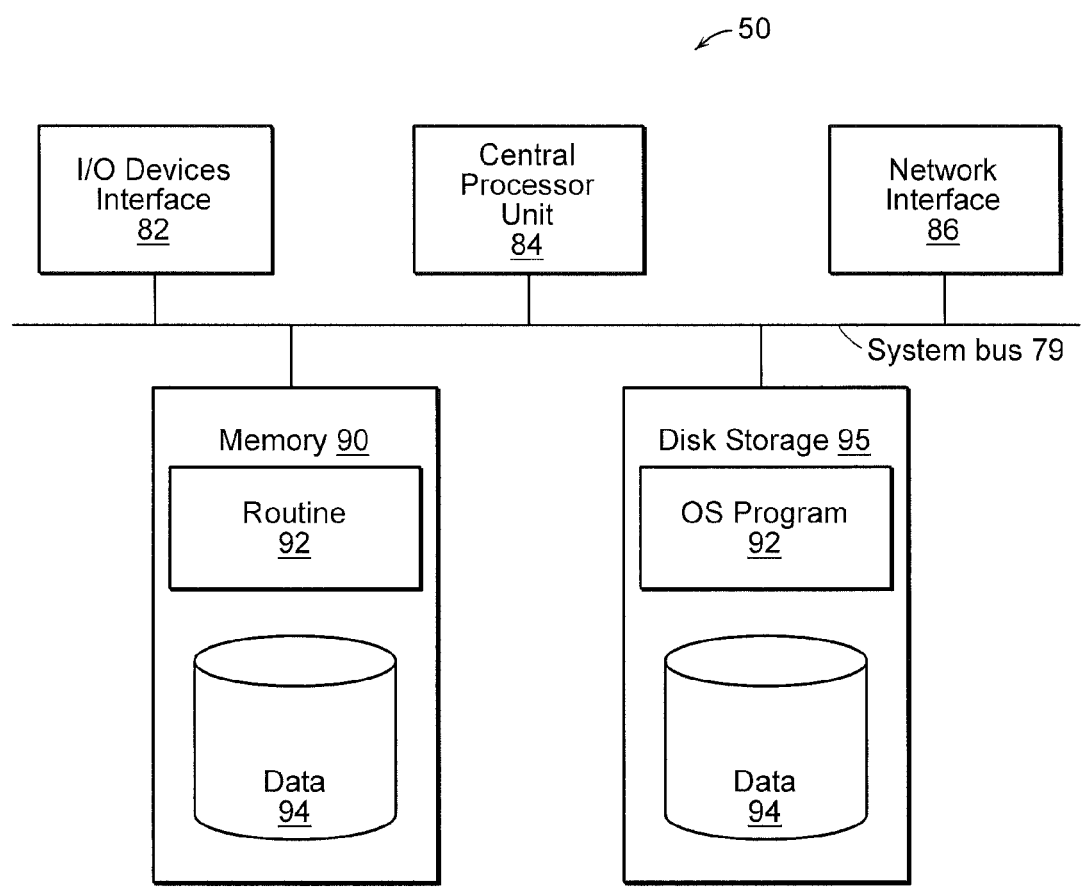
FIG. 10 is a block diagram of a computer apparatus implementing methods of the present invention.

One or more computers 50 execute the program code and can be of a variety of computer architectures such as client-server, standalone processor, networked or distributed processor. FIG. 10 is a diagram of the internal structure of a computer 50 in a computer network or other computer based environment in which the present invention can be implemented. Each computer 50 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50. Network interface 86 allows the computer to connect to various other devices attached to a network (e.g., global computer network, local area network, wide area network, and the like). Memory 90 provides volatile storage for computer software instructions 92 and data 94 used to implement an embodiment of the present invention (e.g., the flowchart shown in FIG. 3 and detailed above). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

EXEMPLIFICATION

Figure 4:
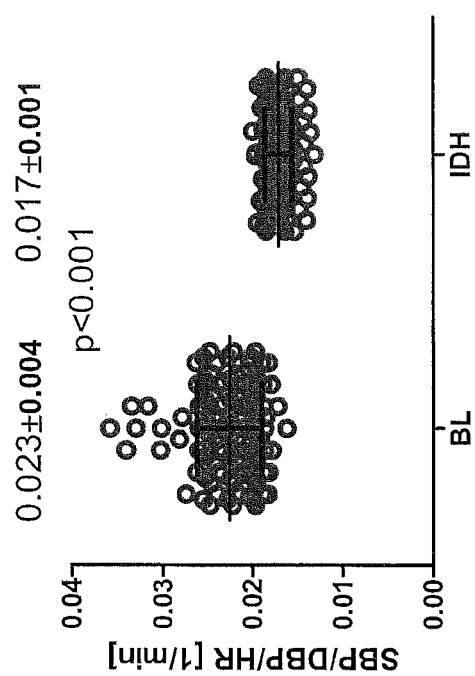
FIG. 4 is a graph of SBP/DBP/HR [1/min], referred herein as the SDH ratio, showing a comparison, for patients that experienced an IME, between an average of the SDH ratio during the first 30 min, when an IME did not occur (thus establishing a baseline (BL)), and the time when an IME occurred, as predicted by the methods according to this invention.
Figure 5:
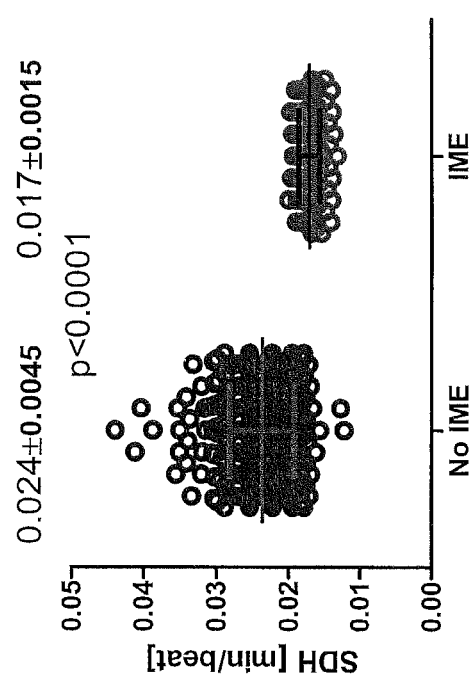
FIG. 5 is a graph of the SDH ratio [min/beat] comparing two groups of patients: no IME and IME.
Figure 6:
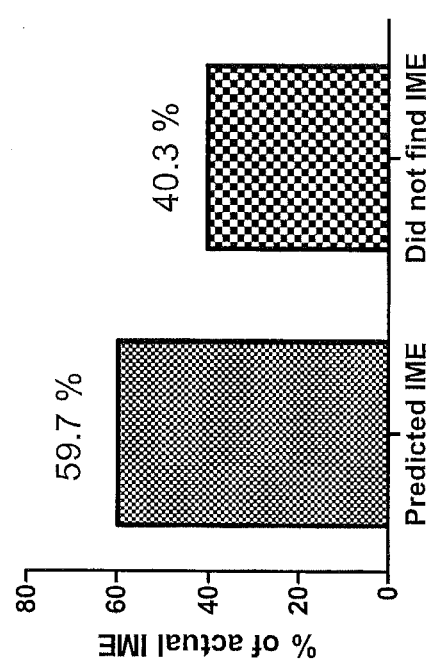
FIG. 6 is a graph of results of a predicted IME using the algorithm combining SDRBV and SDH. 59.7% and 40.3% of actual IMEs (124) were predicted and missed, respectively, by the methods according to this invention.
Figure 7:
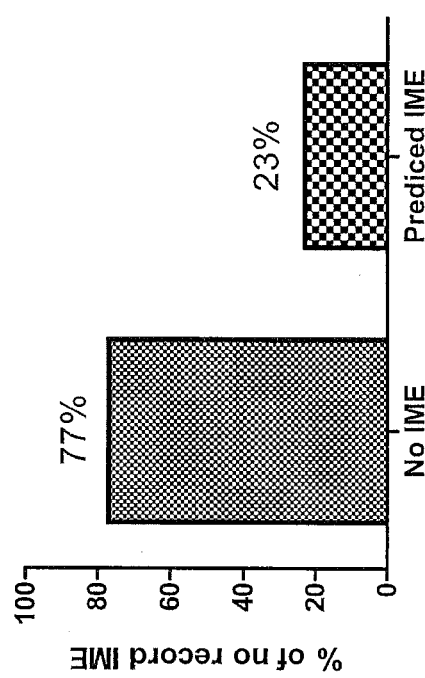
FIG. 7 is a graph of percentage of the number of patients with no IMEs (121) recorded in the study identified (23%) with IME (false positive) by the model. However, 77% of patients with no recorded IMEs (121) were identified as having no IMEs by the methods according to this invention.

Preliminary results were analyzed from 45 patients with 245 measurements (average age 55.7±14 years, average height 167.7±10 cm, average pre-dialysis Wt 79.3±16.6 kg and average post-dialysis Wt 76.3±16 kg) with the algorithm shown in FIG. 3. The average value of SDH was higher in the first 30 minutes of measurement, when no IME occurred (thus providing a baseline (BL)), than in the time when an IME occurred as predicted by the model, as shown in FIG. 4. In a total of 245 treatments, IMEs were recorded in 124 treatments with different aspects of IME such as ultrafiltration (UF) stopped, SBP<90 mmHg and HR>100 beats/min with muscle cramps, dizziness or fainting.

Figure 8:
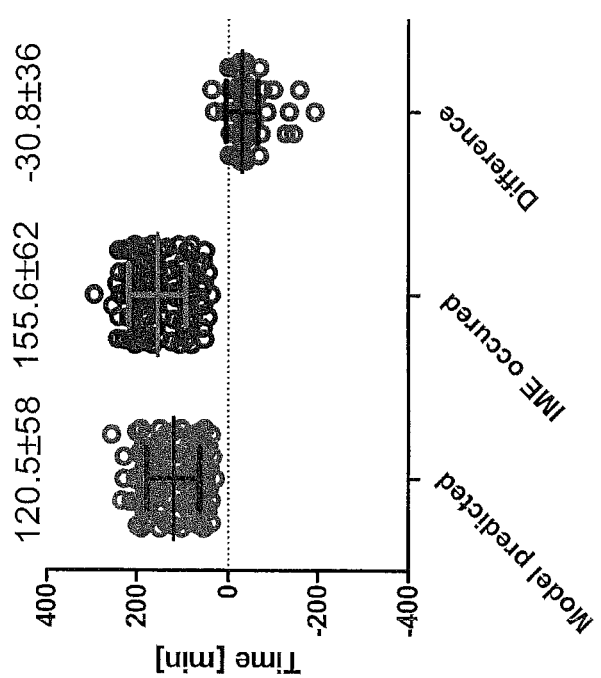
FIG. 8 is a graph showing that the average interval between the prediction and occurrence of an IME time for patient data studied was −30.8±36 minutes with monitoring only SDRBV by the methods according to this invention.
Figure 9:
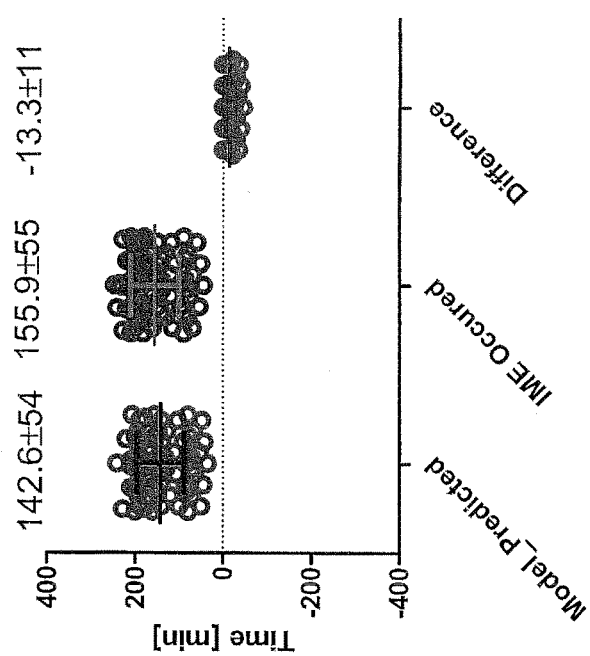
FIG. 9 is a graph showing that the average interval between the prediction and occurrence of an IME time for patient data studied was 13.3±11 minutes with monitoring the combination of SDRBV and SDH by the methods according to this invention.

With the SDRBV model only, as shown in FIG. 8, prediction of the time for the IME is given ahead about 30.8±36 minutes (minimum: −193.4, maximum: 36.1, Q1: −35.6, Q2 (median): −21.8, Q3: −10.4, 95% CI: −38.3~−36.1) before an IME occurred. When using the combination of SDRBV and SDH, as shown in FIG. 9, the prediction of time for an IME to occur was reduced to 13.3±11 minutes (minimum: −45.5, maximum: 0, Q1: −19.8, Q2 (median): −10, Q3: −6.2, 95% CI: −15.9~−10.8), which reflects the reduced variability of predicted time by reducing the coefficient of variation (CV), where CV=standard deviation/mean. The shorter prediction of the time is an acceptable tradeoff for the increase in sensitivity of prediction of an IME from 62.3% by using the SDRBV alone to 72.5% by using the combined SDRBV and SDH. The results are summarized in Table 1. Dotted lines in FIGS. 8 and 9 represent the time when UF was stopped. Each dot represents predicting time of IME by the model in individual treatments. It should be noted that the prediction time is based on the time of IME.

TABLE 1

Summary of prediction of IME with three methods

|  | Number | SDRBV + SDH | | SDRBV only | | SDH only | |
| --- | --- | --- | --- | --- | --- | --- | --- |
|  |  | Yes | No | Yes | No | Yes | No |
| IME | 124 | 74 | 50 | 114 | 10 | 83 | 41 |
| No IME | 121 | 28 | 93 | 69 | 52 | 54 | 67 |
| Sensitivity, % |  | 72.5 |  | 62.3 |  | 60.6 |  |
| Specificity, % |  | 65 |  | 83.9 |  | 38 |  |

Summary (Table 1) of prediction of IMEs with SDRBV, SDH and combination of SDRBV and SDH method shows that the best prediction of IME can be obtained with SDRBV+SDH.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of detecting an indication of a potential intradialytic morbid event (IME) by monitoring a patient's condition during excess fluid removal by ultrafiltration during a hemodialysis treatment, the method comprising:
   i) establishing an initial ultrafiltration rate of fluid removal;
   ii) determining the patient's relative blood volume (RBV);
   iii) removing a portion of the volume of excess fluid from blood of the patient at the initial ultrafiltration rate while periodically monitoring a second derivative of the relative blood volume over time (SDRBV);
   iv) continuing to remove excess fluid from blood of the patient at the same ultrafiltration rate, or incrementally increasing the ultrafiltration rate;
   v) if the SDRBV is in a range of between a low SDRBV alarm level and a high SDRBV alarm level, triggering an alarm for a potential IME for the patient; and
   vi) taking a remedial action if the alarm is triggered.

2. The method of claim 1, wherein the low SDRBV alarm level is about $-0.08\%/min^2$.

3. The method of claim 2, wherein the high SDRBV alarm level is about $-0.035\%/min^2$.

4. The method of claim 3, further including monitoring the patient's normalized blood pressure ratio based on the patient's systolic and diastolic blood pressure and heart rate.

5. The method of claim 4, wherein further including triggering an alarm for a potential IME for the patient if the SDRBV is in a range of between a low SDRBV alarm level and a high SDRBV alarm level and if the normalized blood pressure ratio is less than a ratio alarm level.

6. The method of claim 5, wherein the ratio alarm level is about 0.019 min/beat for a diastolic blood pressure greater than 50 mmHg.

7. The method of claim 5, wherein the ratio alarm level is about 0.02 min/beat for a diastolic blood pressure less than 50 mmHg.

8. The method of claim 1, wherein the remedial action is decreasing the ultrafiltration rate.

9. The method of claim 1, wherein the remedial action is infusion of fluid into the patient.

10. The method of claim 1, wherein the remedial action is increasing pressure on lower extremities of the patient.

11. The method of claim 1, wherein the remedial action is changing the position of the patient.

12. The method of claim 11, wherein the remedial action is selected from placing the patient in the Trendelenburg position and raising the patient's legs.

13. A method of detecting an indication of a potential intradialytic morbid event (IME) by monitoring a patient's condition during excess fluid removal by ultrafiltration during a hemodialysis treatment, the method comprising:
   i) establishing an initial ultrafiltration rate of fluid removal;
   ii) determining the patient's systolic blood pressure (SBP), diastolic blood pressure (DBP), and heart rate (HR);
   iii) removing a portion of the volume of excess fluid from blood of the patient at the initial ultrafiltration rate while periodically monitoring a normalized blood pressure ratio calculated using the patient's systolic and diastolic blood pressure and heart rate data obtained in step ii);
   iv) continuing to remove excess fluid from blood of the patient at the same ultrafiltration rate, or, optionally, incrementally increasing the ultrafiltration rate;
   v) if the ratio is less than a ratio alarm level, triggering an alarm for a potential IME for the patient; and
   vi) taking a remedial action if the alarm is triggered.

14. The method of claim 13, wherein the ratio alarm level is about 0.019 min/beat for a diastolic blood pressure greater than 50 mmHg.

15. The method of claim 14, wherein the ratio alarm level is about 0.02 min/beat for a diastolic blood pressure less than 50 mmHg.

16. The method of claim 15, wherein the remedial action is decreasing the ultrafiltration rate.

17. The method of claim 15, wherein the remedial action is infusion of fluid into the patient.

18. The method of claim 15, wherein the remedial action is increasing pressure on lower extremities of the patient.

19. The method of claim 15, wherein the remedial action is changing the position of the patient.

20. The method of claim 19, wherein the remedial action is selected from placing the patient in the Trendelenburg position and raising the patient's legs.

21. A method of detecting an indication of a potential intradialytic morbid event (IME) by monitoring a patient's condition during excess fluid removal by ultrafiltration during a hemodialysis treatment, the method comprising the computer implemented steps of:
   i) establishing an initial ultrafiltration rate of fluid removal;
   ii) determining the patient's relative blood volume (RBV);
   iii) removing a portion of the volume of excess fluid from blood of the patient at the initial ultrafiltration rate while periodically monitoring a second derivative of the relative blood volume over time (SDRBV);
   iv) continuing to remove excess fluid from blood of the patient at the same ultrafiltration rate, or incrementally increasing the ultrafiltration rate;
   v) if the SDRBV is in a range of between a low SDRBV alarm level and a high SDRBV alarm level, triggering an alarm for a potential IME for the patient; and
   vi) taking a remedial action if the alarm is triggered.

22. The method of claim 21, wherein the low SDRBV alarm level is about $-0.08\%/min^2$.

23. The method of claim 22, wherein the high SDRBV alarm level is about $-0.035\%/min^2$.

24. The method of claim 23, further including monitoring the patient's normalized blood pressure ratio.

25. The method of claim 24, wherein further including triggering an alarm for a potential IME for the patient if the SDRBV is in a range of between a low SDRBV alarm level and a high SDRBV alarm level and if the normalized blood pressure ratio is less than a ratio alarm level.

26. The method of claim 25, wherein the ratio alarm level is about 0.019 min/beat for a diastolic blood pressure greater than 50 mmHg.

27. The method of claim 25, wherein the ratio alarm level is about 0.02 min/beat for a diastolic blood pressure less than 50 mmHg.

28. The method of claim 27, wherein the remedial action is decreasing the ultrafiltration rate.

29. The method of claim 27, wherein the remedial action is infusion of fluid into the patient.

30. The method of claim 27, wherein the remedial action is increasing pressure on lower extremities of the patient.

31. The method of claim 27, wherein the remedial action is changing the position of the patient.

32. The method of claim 31, wherein the remedial action is selected from placing the patient in the Trendelenburg position and raising the patient's legs.

* * * * *